United States Patent [19]

Noltes et al.

[11] 4,228,312

[45] Oct. 14, 1980

[54] HYDROGENATION PROCESS

[75] Inventors: Jan G. Noltes, Huis Ter Heide; J. T. B. H. Jastrzebski, De Bilt; Gerard van Koten, Bilthoven, all of Netherlands

[73] Assignee: Borg-Warner Corporation, Chicago, Ill.

[21] Appl. No.: 18,374

[22] Filed: Mar. 7, 1979

[51] Int. Cl.$^2$ .......................... C07C 5/02; C07C 5/06; C07C 5/08; C07C 5/10

[52] U.S. Cl. .................................... 585/250; 585/259; 585/262; 585/266; 585/267; 585/269; 585/273; 585/277

[58] Field of Search ................ 252/454; 585/262, 266, 585/267, 269, 273, 277, 250, 259

[56] References Cited

U.S. PATENT DOCUMENTS 4,152,303  5/1979  Cohen et al. ......................... 252/454

OTHER PUBLICATIONS

Popov et al., Chem. Ab. 84:73771w.
Alchudzhau et al., Chem. Ab. 71:12280v, 72:66452.
Popov et al., Chem. Ab. 77:18935h.

*Primary Examiner*—Veronica O'Keefe
*Attorney, Agent, or Firm*—Joseph Shekleton

[57] ABSTRACT

A process for the hydrogenation of certain aromatic, olefinic and acetylenic compounds. The process is catalyzed by a zero-valent mixed metal catalyst which is in turn prepared by the reaction of an organic metal cluster compound wherein one of the metals is lithium with a complex of rhodium halide and an olefinic hydrocarbon ligand. The catalyst may, if desired, be deposited on a support such as alumina or silica. The hydrogenation process can, in many instances, be carried out under ordinary conditions, i.e., at room temperature and atmospheric pressure.

6 Claims, No Drawings

HYDROGENATION PROCESS

The invention of this application relates to a hydrogenation process. More particularly, it relates to the catalysis of such a process by a certain zero-valent mixed metal catalyst; the catalyst is effective to promote the hydrogenation of aromatic, olefinic and acetylenic compounds.

Popov et al., C.A. 84: 73771w, suggest that the effextiveness of a rhodium-alumina catalyst in the hydrogenation of benzene is directly proportional to the proportion of rhodium in the catalyst. The temperature of the hydrogenation ranges from 100° C. to 160° C.

Alchudzhan et al., C.A. 71: 12280v, studied the temperature dependence of the rate of benzene hydrogenation on a rhodium/silica catalyst. The activity was studied at 200° C., 160° C., 140° C., 115° C., 90° C. and 70° C. The activity-temperature curve showed a maximum at 110° C. Also, the activity of Group VIII metals was shown to decrease in the series rhodium > ruthenium > platinum > palladium.

Alchudzhan et al., C.A. 72: 66452s, show the catalysis of benzene hydrogenation by a silver rhodium mixture and also by a rhodium gold mixture.

Popov et al., C.A. 77: 18935h, show the hydrogenation of benzene in the presence of several mixed catalysts including platinum-ruthenium, rhodium-ruthenium, platinum-palladium, palladium-rhodium and platinum-rhodium. At 160° C., the most effective catalyst was found to be a 90:10 palladium-ruthenium mixture.

The preparation of zero-valent mixed metal catalysts from aromatic metal cluster compounds is shown in copending application Ser. No. 827,278, filed Aug. 24, 1977, now U.S. Pat. No. 4,152,303.

The catalyst employed in the process of the present invention is a zero-valent mixed metal composition prepared by reacting an organic metal cluster compound wherein one of the metals of said cluster compound is lithium, with a metal halide complex of the formula $RhX_aL_b$ wherein X is chlorine or bromine, L is an olefinic hydrocarbon ligand, a is 1-3 and b is 1-4, in a hydrocarbon solvent. The process preferably is carried out in a dry, oxygen-free atmosphere. The atmosphere may be, e.g., nitrogen, ethylene or argon.

The metal cluster compound also contains, in addition to lithium, a Group IB metal. Gold is preferred although silver and copper are also quite satisfactory. A third metal may, in some instances, be present also. Thus, a metal cluster compound may contain lithium, and two different Group IB metals; other metals may also be present although in the more usual cases only two metals will be present, one being lithium and the other a Group IB metal. The composition of the metal cluster compound may be shown by the formula $R_{x+y}M_xLi_y$ where R is alkyl of 1-12 carbon atoms, M is a Group IB metal, x and y are 1-4, and x+y is 2-8. Preferably, x+y is 4, and x=y=2.

The metal halide complex is as indicated a rhodium halide complex. The halide may be chlorine or bromine. Chlorine is preferred. The olefinic hydrocarbon ligand is construed broadly; specific illustrative embodiments include ethylene, 1,5.cyclooctadiene, 1,7.norbornadiene, butene-1 and hexene-1. Olefinic hydrocarbons having up to 12 carbon atoms are contemplated. Examples of metal halide complexes include $RhCl(CH_2{=}CH_2)_2$, RhBr.cyclooctadiene, RhCl.norbornadiene, etc.

The process is carried out very simply, merely by mixing the reactants at room temperture, i.e., from about 20° C. to about 30° C. A reaction occurs at once. The zero-valent metal product may be used as such in a catalytic hydrogenation, or it may be deposited on a support and isolated by decanting the hydrocarbon solvent away from the solid product. The support may be any of those commonly used in catalytic chemistry, viz., alumina, silica, clay and the like.

The process is carried out in a solvent. The reactants may not be completely soluble in the solvent, and the zero-valent mixed metal product is not soluble, so that agitation of the process mixture is highly desirable. Suitable solvents include benzene, toluene, xylene, ethylbenzene, pentane, cyclohexane and, in fact, any hydrocarbon solvent which is normally liquid, i.e., liquid at about room temperature.

The reaction of the process is illustrated by the following equation:

It will be noted that rhodium is one of the metals of the zero-valent mixed metal catalyst herein.

The hydrogenation reactions of the invention which are catalyzed by the zero-valent metal products herein may, in most instances, be carried out at room temperature and at ordinary pressures. Aromatic compounds, i.e., the aromatic ring, can be hydrogenated merely by introducing hydrogen into a reaction vessel containing the aromatic compound and the catalyst. Benzene and naphthalene, for example, can be hydrogenated in this fashion, benzene yielding cyclohexane and naphthalene yielding a mixture of cis- and trans-decalin. Similarly, the hydrogenation of phenol, anisole and methyl benzoate yields cyclohexanol, methylcyclohexylether and methylcyclohexanoate, respectively. Olefinic compounds can also be hydrogenated under similar conditions. Styrene, for example, can be converted to ethylbenzene and then to ethylcyclohexane. Stilbene can be converted to 1,2-diphenylethane and then to 1,2-dicyclohexylethane. Phenylacetylene can be hydrogenated likewise to ethylbenzene, and then to ethylcyclohexane.

At the same time, the effectiveness of the zero-valent mixed metal catalysts herein is considerably diminished by compounds which are known to form strong complexes with metals. Attempts to hydrogenate benzonitrile, for example, at room temperature and atmospheric pressure, are unsuccessful. The same is true of N,N-dimethylaniline, triphenylphosphine, triphenylphosphine oxide, and thioanisole.

These zero-valent mixed metal catalysts are characterized by unusual catalytic effectiveness in hydrogenation reactions. They are more effective, for example, than the zero-valent catalysts prepared by the process described in U.S. application Ser. No. 827,278, filed Aug. 24, 1977 now U.S. Pat. No. 4,152,303. In that process an aromatic metal cluster compound is used as the reactant source of the Group IB metal instead of the aliphatic metal cluster compound of the present hydrogenation process.

The organic metal cluster compounds may be prepared as follows. An alkyl lithium compound such as n-butyl lithium is reacted with half an equivalent amount of cuprous halide, for example, to form a metal cluster product whose composition is indicated by the formula $R_4Cu_2Li_2$. The R, which represents n-butyl in such a metal cluster compound, for example, may also be methyl, ethyl, n-propyl, sec-butyl, isobutyl, tert-butyl, n-pentyl, n-hexyl, 2-methylpentyl, 2-ethylhexyl, n-decyl, etc. The method of preparation of these metal cluster compounds is illustrated in Example 1.

EXAMPLE 1

To a stirred suspension of 4.94 g. (10 mmols) of gold chloride-triphenylphosphine complex (AuCl.P(Ph)$_3$) in 100 ml. of pentane containing about 1.1 g. (15 mmols) of diethylether, there is added 1.28 g. (20 mmols) of n-butyllithium. The reaction mixture develops a yellow color and a white precipitate forms. The mixture is chilled to −80° C. and the yellow liquid is decanted from the solid; the solid is identified by its 'H-NMR spectrum in C$_6$D$_6$ as triphenylphosphine. The yellow pentane solution is evaporated at 50° C./0.1 mm. Hg, yielding a yellow-brown oil. Its 'H-NMR spectrum in C$_6$D$_6$ shows butyl and ether signals in a 2:1 ratio, which is consistent with the structure of the organic metal cluster compound n-Bu$_2$AuLi.Et$_2$O. This product is thus isolated in a 98% yield. It is sensitive to hydrolysis and oxidation.

The process by which the mixed metal catalysts employed in the present invention may be prepared utilizes a metal cluster compound such as that prepared by the procedure of Example 1 as a starting material. An illustrative embodiment is shown in Example 2.

EXAMPLE 2

To a 0.5 M solution in benzene of 391 mg. (1 mmol) of di-n-butylgoldlithium monoetherate (Bu$_2$AuLi.Et$_2$O) under nitrogen, there is added 194 mg. (1 mmol) of rhodium chloride-ethylene complex (RhCl.(CH$_2$=CH$_2$)$_2$). A metallic deposit Au$^0$/Rh$^0$ is formed almost at once. Its effectiveness as a hydrogenation catalyst is determined by hydrogenating benzene to cyclohexene at room temperature and atmospheric pressure. Under these conditions the above Au$^0$/Rh$^0$ material causes the hydrogenation to proceed at the rate of 1.6 mmol/min/mmol of catalyst.

A similar Au$^0$/Rh$^0$ prepared from an aromatic metal cluster compound, viz., (p-tol)$_4$Au$_2$Li$_2$.(Et$_2$O)$_2$, causes the hydrogenation of benzene to proceed under identical conditions at a rate of 0.7 mmol/min/mmol of catalyst.

A similar Au$^0$/Rh$^0$ prepared by the process of this invention, but from a rhodium chloride.cyclooctadiene complex rather than the rhodium chloride.ethylene complex of the above example, showed the identical catalytic effectiveness, i.e., a hydrogenation (of benzene, at room temperature and atmospheric pressure) rate of 1.6 mmol/min/mmol of catalyst.

Naphthalene, stilbene, styrene, phenylacetylene and other aromatic, olefinic and acetylenic compounds may be hydrogenated similarly.

All parts and percentages herein are by weight unless otherwise expressly stated.

We claim:

1. A process for the hydrogenation of aromatic, olefinic and acetylenic compounds comprising treating such compounds, which contain no nitrogen, phosphorous, tin or halogen, with hydrogen in the presence of a zero-valent mixed metal catalyst prepared by reacting an aliphatic metal cluster compound of the formula R$_{x+y}$M$_x$Li$_y$ where R is alkyl of 1–12 carbon atoms, M is a Group IB metal, x and y are each 1–4, and x+y is 2–8, with a metal halide complex of the formula RhX$_a$L$_b$ wherein X is chlorine or bromine, L is an olefinic hydrocarbon ligand, a is 1–3 and b is 1–4, in a hydrocarbon solvent.

2. The process of claim 1 wherein the hydrogenation is carried out at about room temperature.

3. The process of claim 1 wherein the hydrogenation is carried out at about atmospheric pressure.

4. The process of claim 1 wherein the aliphatic metal cluster compound is an alkylgoldlithium.

5. The process of claim 1 wherein the metal halide complex is a rhodium chloride complex.

6. The process of claim 5 wherein the ligand of the rhodium chloride complex is ethylene.

* * * * *